(12) United States Patent
Peduto et al.

(10) Patent No.: US 9,777,276 B2
(45) Date of Patent: Oct. 3, 2017

(54) ADAM12 INHIBITORS AND THEIR USE AGAINST INFLAMMATION-INDUCED FIBROSIS

(71) Applicant: Institut Pasteur, Paris (FR)

(72) Inventors: Lucie Peduto, Paris (FR); Gerard Eberl, Paris (FR)

(73) Assignee: INSTITUT PASTEUR, Paris (FR)

( * ) Notice: Subject to any disclaimer, the term of this patent is extended or adjusted under 35 U.S.C. 154(b) by 1 day.

(21) Appl. No.: 14/479,006

(22) Filed: Sep. 5, 2014

(65) Prior Publication Data
US 2015/0005367 A1    Jan. 1, 2015

Related U.S. Application Data

(62) Division of application No. 13/393,113, filed as application No. PCT/IB2010/053865 on Aug. 27, 2010, now abandoned.

(30) Foreign Application Priority Data

Aug. 28, 2009 (CA) ..................................... 2676946

(51) Int. Cl.

| | |
|---|---|
| *A61K 39/395* | (2006.01) |
| *A61K 39/00* | (2006.01) |
| *C12N 15/113* | (2010.01) |
| *A61K 38/48* | (2006.01) |
| *G01N 33/573* | (2006.01) |
| *G01N 33/68* | (2006.01) |
| *A01K 67/027* | (2006.01) |
| *C12Q 1/68* | (2006.01) |
| *C12N 15/85* | (2006.01) |

(52) U.S. Cl.
CPC ...... *C12N 15/1137* (2013.01); *A01K 67/0275* (2013.01); *A61K 38/4886* (2013.01); *C12Q 1/6883* (2013.01); *C12Q 1/6897* (2013.01); *G01N 33/573* (2013.01); *G01N 33/6893* (2013.01); *A01K 2217/203* (2013.01); *A01K 2217/206* (2013.01); *A01K 2227/105* (2013.01); *A01K 2267/0368* (2013.01); *A01K 2267/0393* (2013.01); *C12N 15/8509* (2013.01); *C12N 2015/859* (2013.01); *C12N 2310/14* (2013.01); *C12N 2320/30* (2013.01); *C12N 2800/107* (2013.01); *C12N 2820/55* (2013.01); *C12Q 2600/158* (2013.01); *G01N 2333/96486* (2013.01); *G01N 2500/00* (2013.01); *G01N 2800/085* (2013.01); *G01N 2800/12* (2013.01); *G01N 2800/382* (2013.01)

(58) Field of Classification Search
None
See application file for complete search history.

(56) References Cited

U.S. PATENT DOCUMENTS

| 2009/0181941 A1* | 7/2009 | Leblanc | ............... C07D 471/04 |
| | | | 514/210.21 |
| 2011/0256054 A1* | 10/2011 | Menko | ................... C07K 16/30 |
| | | | 424/1.11 |

FOREIGN PATENT DOCUMENTS

| EP | 0 342 682 | 11/1989 |
| WO | 97/40072 | 10/1997 |
| WO | 2006/014903 | 2/2006 |

OTHER PUBLICATIONS

Shah M, Foreman DM, Ferguson MW: Neutralising antibody to TGF-beta 1,2 reduces cutaneous scarring in adult rodents. J Cell Sci. 1994, 107: 1137-1157.*
Leask, A. Matrix contraction by dermal fibroblasts requires syndecan 4: Insights into pathological scarring in chronic fibrotic disease. In: FASEB Journal. (2006, 20:A1098).*
Engvall et al. The new frontier in muscular dystrophy research: booster genes. (FASEB Journal (2003), 17(12), 1579-1584).*
Moghadaszadeh et al. Compensation for dystrophin-deficiency: ADAM12 overexpression in skeletal muscle results in increased alpha 7 integrin, utrophin and associated glycoproteins. Hum Mol Genet Oct. 1, 2003;12(19):2467-79.*
Kronqvist al. ADAM12 Alleviates the Skeletal Muscle Pathology in mdx Dystrophic Mice. American Journal of Pathology, vol. 161(5):1535-1540, Nov. 2002.*
Paulissen, Expression of ADAMs and Their Inhibitors in Sputum from Patients with Asthma, Molecular Medicine, 12, pp. 171-179, 2006.
Jorgensen, Transgenic Overexpression of ADAM12 Suppresses Muscle Regeneration and Aggravates Dystrophy in ages mdx Mice, The American Journal of Pathology, 171 pp. 1599-1607, 2007.
Le Pabic et al. ADAM 12 in Human Liver Cancers: TGF-a-Regulated Expression in Stellate Cells Is Associated With Matrix Remodeling. Hepatology 2003;37:1056-1066.
Bourd-Boittin et al (2008). Rack1, a new ADAM12 interacting protein. Contribution to liver fibrogenesis, J. Bioi. Chem. 283, 26000-26009.
Dulauroy et al. Lineage tracing and genetic ablation of ADAM12+ perivascular cells identify a major source of profibrotic cells during acute tissue injury. Nature medicine, 18(8), 1262-1270 , Aug. 2012.

\* cited by examiner

*Primary Examiner* — Maher Haddad
(74) *Attorney, Agent, or Firm* — Arrigo, Lee & Guttman LLP

(57) ABSTRACT

The present invention relates to the field of fibrosis and inflammation and more particularly to the use of ADAM12 (A Disintegrin and Metalloproteinase 12) inhibitors to prevent or treat inflammation-induced fibrosis. The present invention also relates to the use of ADAM12 as a marker for inflammation-induced fibrosis and to the ablation of ADAM12 expressing cells as therapeutic approach to interfere with the development of pro-fibrotic cells.

6 Claims, 10 Drawing Sheets

Figure 5

Sequence CRE-IRES-EGFP-flag 2369bp

ATGTCCAATTTACTGACCGTACACCAAAATTTGCCTGCATTACCGGTCGATGCAACGAGT
GATGAGGTTCGCAAGAACCTGATGGACATGTTCAGGGATCGCCAGGCGTTTTCTGAGCA
TACCTGGAAAATGCTTCTGTCCGTTTGCCGGTCGTGGGCGGCATGGTGCAAGTTGAATA
ACCGGAAATGGTTTCCCGCAGAACCTGAAGATGTTCGCGATTATCTTCTATATCTTCAGG
CGCGCGGTCTGGCAGTAAAAACTATCCAGCAACATTTGGGCCAGCTAAACATGCTTCAT
CGTCGGTCCGGGCTGCCACGACCAAGTGACAGCAATGCTGTTTCACTGGTTATGCGGC
GGATCCGAAAGAAAACGTTGATGCCGGTGAACGTGCAAAACAGGCTCTAGCGTTCGAA
CGCACTGATTTCGACCAGGTTCGTTCACTCATGGAAAATAGCGATCGCTGCCAGGATATA
CGTAATCTGGCATTTCTGGGGATTGCTTATAACACCCTGTTACGTATAGCCGAAATTGCC
AGGATCAGGGTTAAAGATATCTCACGTACTGACGGTGGGAGAATGTTAATCCATATTGGC
AGAACGAAAACGCTGGTTAGCACCGCAGGTGTAGAGAAGGCACTTAGCCTGGGGGTAA
CTAAACTGGTCGAGCGATGGATTTCCGTCTCTGGTGTAGCTGATGATCCGAATAACTACC
TGTTTTGCCGGGTCAGAAAAAATGGTGTTGCCGCGCCATCTGCCACCAGCCAGCTATCA
ACTCGCGCCCTGGAAGGGATTTTTGAAGCAACTCATCGATTGATTTACGGCGCTAAGGAT
GACTCTGGTCAGAGATACCTGGCCTGGTCTGGACACAGTGCCCGTGTCGGAGCCGCGC
GAGATATGGCCCGCGCTGGAGTTTCAATACCGGAGATCATGCAAGCTGGTGGCTGGAC
CAATGTAAATATTGTCATGAACTATATCCGTAACCTGGATAGTGAAACAGGGGCAATGGT
GCGCCTGCTGGAAGATGGCGATTAGTGCGCGCCGCCCTCTCCCTCCCCCCCCCTAA
CGTTACTGGCCGAAGCCGCTTGGAATAAGGCCGGTGTGCGTTTGTCTATATGTTATTTTC
CACCATATTGCCGTCTTTTGGCAATGTGAGGGCCCGGAAACCTGGCCCTGTCTTCTTGA
CGAGCATTCCTAGGGGTCTTTCCCCTCTCGCCAAAGGAATGCAAGGTCTGTTGAATGTC
GTGAAGGAAGCAGTTCCTCTGGAAGCTTCTTGAAGACAAACAACGTCTGTAGCGACCCT
TTGCAGGCAGCGGAACCCCCCACCTGGCGACAGGTGCCTCTGCGGCCAAAAGCCACGT
GTATAAGATACACCTGCAAAGGCGGCACAACCCCAGTGCCACGTTGTGAGTTGGATAGT
TGTGGAAAGAGTCAAATGGCTCTCCTCAAGCGTATTCAACAAGGGGCTGAAGGATGCCC
AGAAGGTACCCCATTGTATGGGATCTGATCTGGGGCCTCGGTGCACATGCTTTACATGT
GTTTAGTCGAGGTTAAAAAAACGTCTAGGCCCCCCGAACCACGGGGACGTGGTTTTCCT
TTGAAAAACACGATGATAATATGGCCACAACCATGGTGAGCAAGGGCGAGGAGCTGTTC
ACCGGGGTGGTGCCCATCCTGGTCGAGCTGGACGGCGACGTAAACGGCCACAAGTTCA
GCGTGTCCGGCGAGGGCGAGGGCGATGCCACCTACGGCAAGCTGACCCTGAAGTTCAT
CTGCACCACCGGCAAGCTGCCCGTGCCCTGGCCCACCCTCGTGACCACCCTGACCTAC
GGCGTGCAGTGCTTCAGCCGCTACCCCGACCACATGAAGCAGCACGACTTCTTCAAGTC
CGCCATGCCCGAAGGCTACGTCCAGGAGCGCACCATCTTCTTCAAGGACGACGGCAAC
TACAAGACCCGCGCCGAGGTGAAGTTCGAGGGCGACACCCTGGTGAACCGCATCGAGC
TGAAGGGCATCGACTTCAAGGAGGACGGCAACATCCTGGGGCACAAGCTGGAGTACAA
CTACAACAGCCACAACGTCTATATCATGGCCGACAAGCAGAAGAACGGCATCAAGGTGA
ACTTCAAGATCCGCCACAACATCGAGGACGGCAGCGTGCAGCTCGCCGACCACTACCA
GCAGAACACCCCCATCGGCGACGGCCCCGTGCTGCTGCCCGACAACCACTACCTGAGC
ACCCAGTCCGCCCTGAGCAAAGACCCCAACGAGAAGCGCGATCACATGGTCCTGCTGG
AGTTCGTGACCGCCGCGGGATCACTCTCGGCATGGACGAGCTGTACAAGGATTACAAG
GATGACGACGATAAG

CRE 1032bp
IRES Clontech 581bp
EGFP-N1 Clontech 720bp
FLAG 24bp

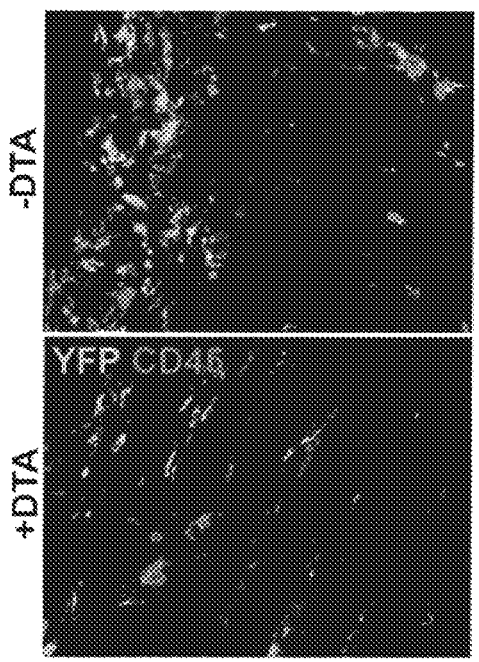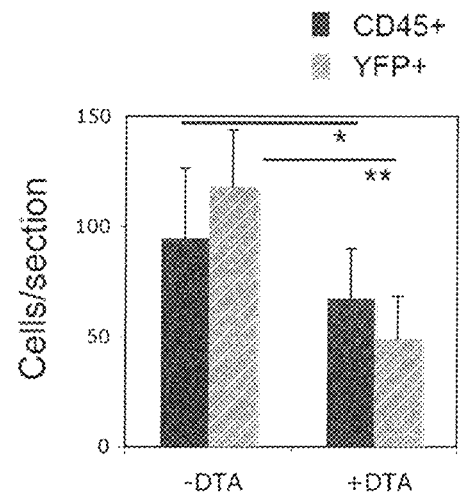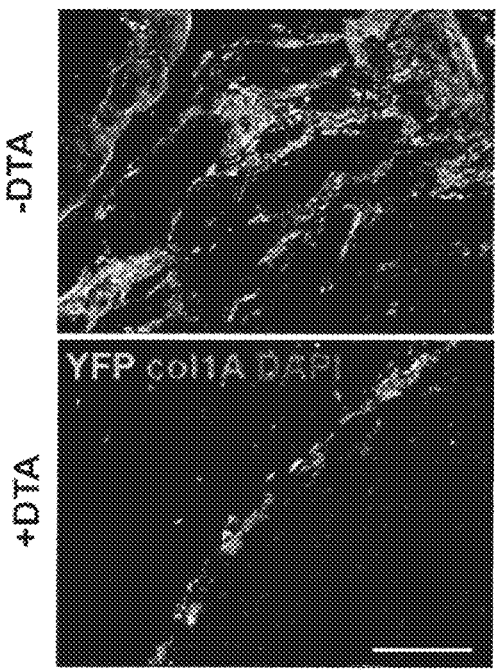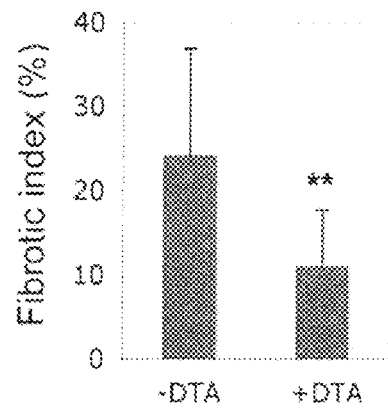
Figure 6

ADAM12 INHIBITORS AND THEIR USE AGAINST INFLAMMATION-INDUCED FIBROSIS

SEQUENCE LISTING SUBMISSION VIA EFS-WEB

A computer readable text file, entitled "045636-5186-01_Sequence-Listing.txt," created on or about Sep. 2, 2012, with a file size of about 4 kb contains the sequence listing for this application and is hereby incorporated by reference in its entirety.

FIELD OF THE INVENTION

The present invention relates to the field of fibrosis and inflammation and inflammation-induced fibrosis and more particularly to the use of ADAM12 (A Disintegrin and Metalloproteinase 12) inhibitors to prevent or treat inflammation-induced fibrosis. The present invention also relates to the use of ADAM12 as a marker for the inflammation-induced fibrosis. The present invention further relates to the ablation of ADAM12-expressing cells as a therapeutic approach for interfering with the development of pro-fibrotic cells.

BACKGROUND OF THE INVENTION

Tissue injury initiates a scarring process involving stromal cell activation and expansion. Initially beneficial, persistent stromal cell activation and proliferation generate pro-fibrotic cells and accumulation of extracellular matrix, which compromises organ recovery. Inflammation is an important initiator of the fibrosis but the cellular origin of pro-fibrotic stromal cells and their mechanism of activation remain unclear.

During inflammation, stromal cells regulate lymphocyte recruitment and survival through the secretion of specific chemokines and cytokines, resulting eventually in the clearance of inflammation, this phase is usually named the acute phase of inflammation. Disruption of this homeostasis can lead to chronic inflammation and its corollary of severe illnesses, such as tissue fibrosis.

Fibrosis is the formation of excess fibrous connective tissue during the reparative and reactive process following tissue damage and inflammation. As major components of fibrosis, pro-fibrotic stromal cells play a critical role in the maintenance of chronic inflammation and often preclude full organ recovery, and in some cases can induce organ failure. This can lead to severe illnesses of major impact on public health such as liver cirrhosis, scleroderma, heart and pulmonary fibrosis, atherosclerosis, and asthma. The formation of tissue fibrosis is currently considered to be an irreversible process, which is poorly modulated by anti-inflammatory and immunosuppressive drugs. The mechanisms leading to the formation of tissue fibrosis has remained elusive and therefore has prevented the elaboration of an adequate therapeutic treatment.

The inventors have described previously the emergence of a stromal population of cells (gp38+ lymphoid stromal cells) that massively proliferate and provide key survival, chemotactic and morphogenic factors for the development of lymphocyte permissive tissue during ontogeny and inflammation (Peduto et al., Journal of Immunology, 2009, 182:5789-5799). They have shown that these stromal cells are not recruited from circulating precursors but develop from tissue-resident cells that remained to be characterized.

ADAMs (A Disintegrin And Metalloproteinase) are a family of cell surface multidomain proteins having key roles in the ectodomain shedding and processing of growth factors, cytokines, receptors, adhesion molecules and other molecules from the plasma membrane. This process has emerged as an important posttranslational regulator of the function of many cleaved substrate proteins, including EGF-receptor ligands and TNFα. In addition to protease activity, several ADAMs possess cell binding and cell signalling properties due to their non-catalytic domains. More than 30 members have been identified in the ADAM family with a broad tissue distribution and have been involved in several cellular processes. Due to their ability to rapidly affect key signalling activities between cells and their environment, ADAM family members could conceivably contribute to pathogenesis including tumorigenesis, especially if their function is dysregulated. Therefore, they are making up the majority of pharmaceutical targets currently undergoing preclinical and clinical evaluation (Moss et al., "ADAMs: Targets for Drug Discovery", Current Pharmaceutical Design, 2009, 15(20):2270-1).

ADAM12 is an active protease involved in the Epidermal Growth Factor Receptor (EGFR) and insulin-like growth factor (IGF) receptor signalling, and plays a role in tumor progression (Peduto et al., Oncogene, 2006, 25:5462-5466). ADAM12 is also involved in several diseases such as arthrosis, cardiac hypertrophy and neurodegenerative diseases (Jacobsen & Wewer, Current Pharmaceutical Design, 2009, 15: 2300-2310).

There is still a need to provide tools, markers and inhibitors for inflammation induced fibrosis.

SUMMARY OF THE INVENTION

The present invention provides new tools for the prevention, treatment and diagnosis of fibrosis. In one aspect, the present invention concerns the use of an ADAM12 inhibitor for preventing and/or treating inflammation-induced fibrosis.

Yet another object of the invention concerns a composition for preventing or treating inflammation-induced fibrosis comprising an ADAM12 inhibitor and a pharmaceutically acceptable carrier.

Another aspect of the invention is a method for preventing or treating inflammation-induced fibrosis in a subject, comprising the step of administering the composition as defined above to the subject.

In another aspect, the present invention provides the use of ADAM12 as an early marker for inflammation-induced fibrosis.

In another aspect, the present invention provides the use of ADAM12 as a marker for activated stromal cells involved in inflammation-induced fibrosis.

In another aspect, the present invention provides a method for diagnosing inflammation-induced fibrosis in a subject, comprising:
  detecting the expression of ADAM12 gene in stromal cells from a biological sample of said subject, and
  relating the expression of ADAM12 gene to the presence or the advent of inflammation-induced fibrosis.

In another aspect, the present invention provides a method for diagnosing inflammation-induced fibrosis in a subject, comprising:
  determining the level of ADAM12 gene expression in stromal cells from a biological sample of said subject, and comparing this level with a reference level, whereby an increased level of ADAM12 gene expression in said stromal cells with respect to the reference level indicating the presence or the advent of inflammation-induced fibrosis.

The present invention also concerns a method for detecting stromal cells activated upon tissue injury and inflammation and that will generate pro-fibrotic cells by detecting ADAM12 expression in the stromal cells, and relating the expression of ADAM12 gene to the presence of these activated stromal cells.

The present invention also concerns a bacterial strain comprising a generated bacterial artificial chromosome (BAC) expressing a Cre recombinase and a fluorescent reporter EGFP under control of the Adam12 gene, deposited on Aug. 28, 2009 under No I-4225 at the CNCM.

In another aspect, the invention provides a transgenic mouse comprising the BAC contained in the bacterial strain of the invention.

Still another object of the invention is to provide a screening method for identifying ADAM12 inhibitors, comprising the steps of:
  inducing an inflammation response at a desired site of the transgenic mouse of the invention,
  applying at the site of inflammation a candidate compound to be tested,
  evaluating expression of the fluorescent reporter EGFP polypeptide; and
  identifying that the expression level of said fluorescent reporter EGFP is inhibited, therefore indicating that the candidate compound has the capacity of inhibiting the ADAM12 gene expression.

Another object of the invention concerns a cytotoxic compound able to specifically kill ADAM12 expressing stromal cells for use to prevent or treat fibrosis, wherein said compound comprises a targeting molecule selected among an antibody or a small interfering RNA specific for ADAM12, and a cytotoxic molecule which is a toxin.

Yet another object of the invention concerns a composition for preventing or treating inflammation-induced fibrosis comprising a cytotoxic compound targeting ADAM12 expressing cells to kill them and a pharmaceutically acceptable carrier. Such compound includes specific antibodies against ADAM12 coupled to a toxin.

The invention concerns also the use of the described transgenic mouse as a tool to detect activated stromal cells, as defined by the expression of ADAM12, during acute or chronic inflammation, and more generally in fibrosis-related diseases.

In another aspect, the present invention provides the use of ADAM12 as a target to specifically kill stromal cells activated by inflammation and generating pro-fibrotic cells.

M: muscle; F: fibrosis; CFA: complete Freud's adjuvant; CX: cardiotoxin; GFP: green fluorescent protein; RFP: red fluorescent protein; α-SMA: alpha Smooth Muscle Actin; dapi labels nuclei.

Figure 3:
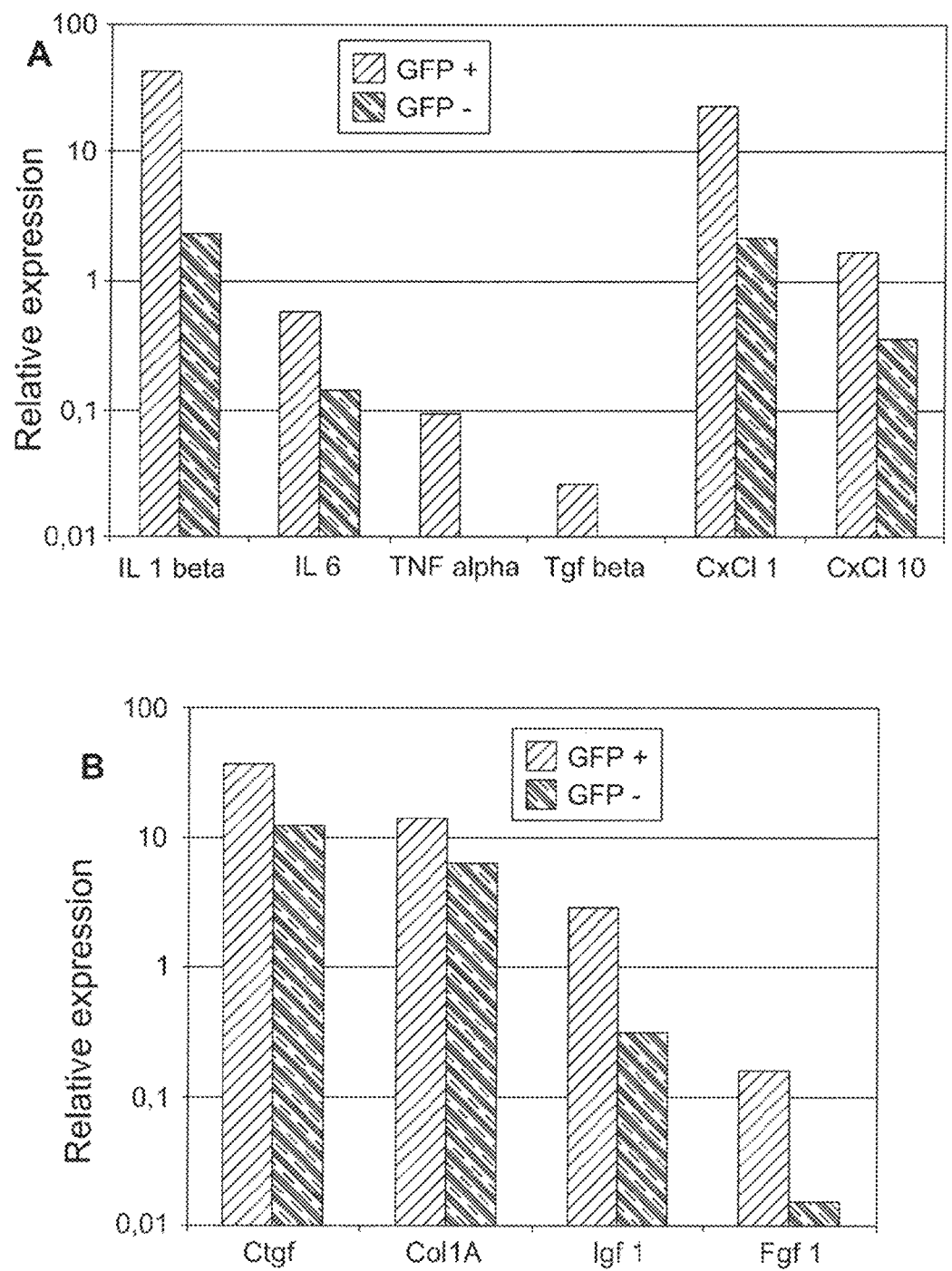

FIG. 3. Gene expression analysis by qRT-PCR of FACS-sorted GFP+ cells generated during inflammation. IL1beta, IL6, TNF alpha, TGF beta, CxCl 1, CxCl 10 in (A), and Ctgf, Col1A, IGF 1, FGF 1 in (B).

Figure 4:
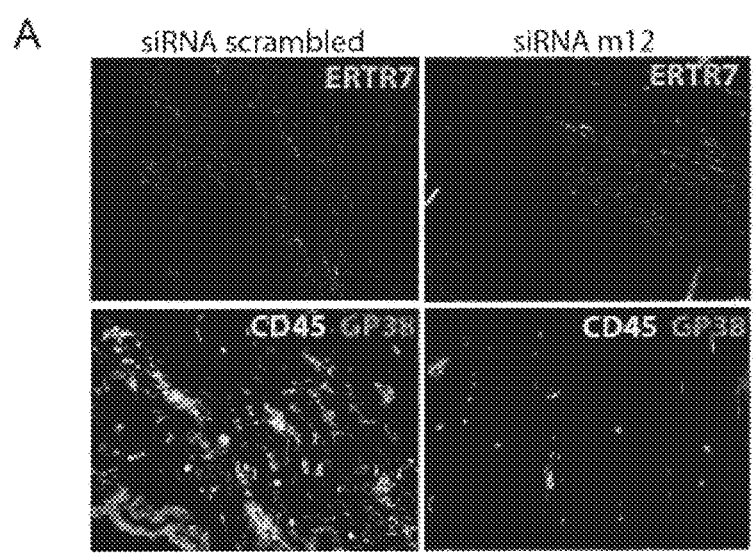
Figure 4:
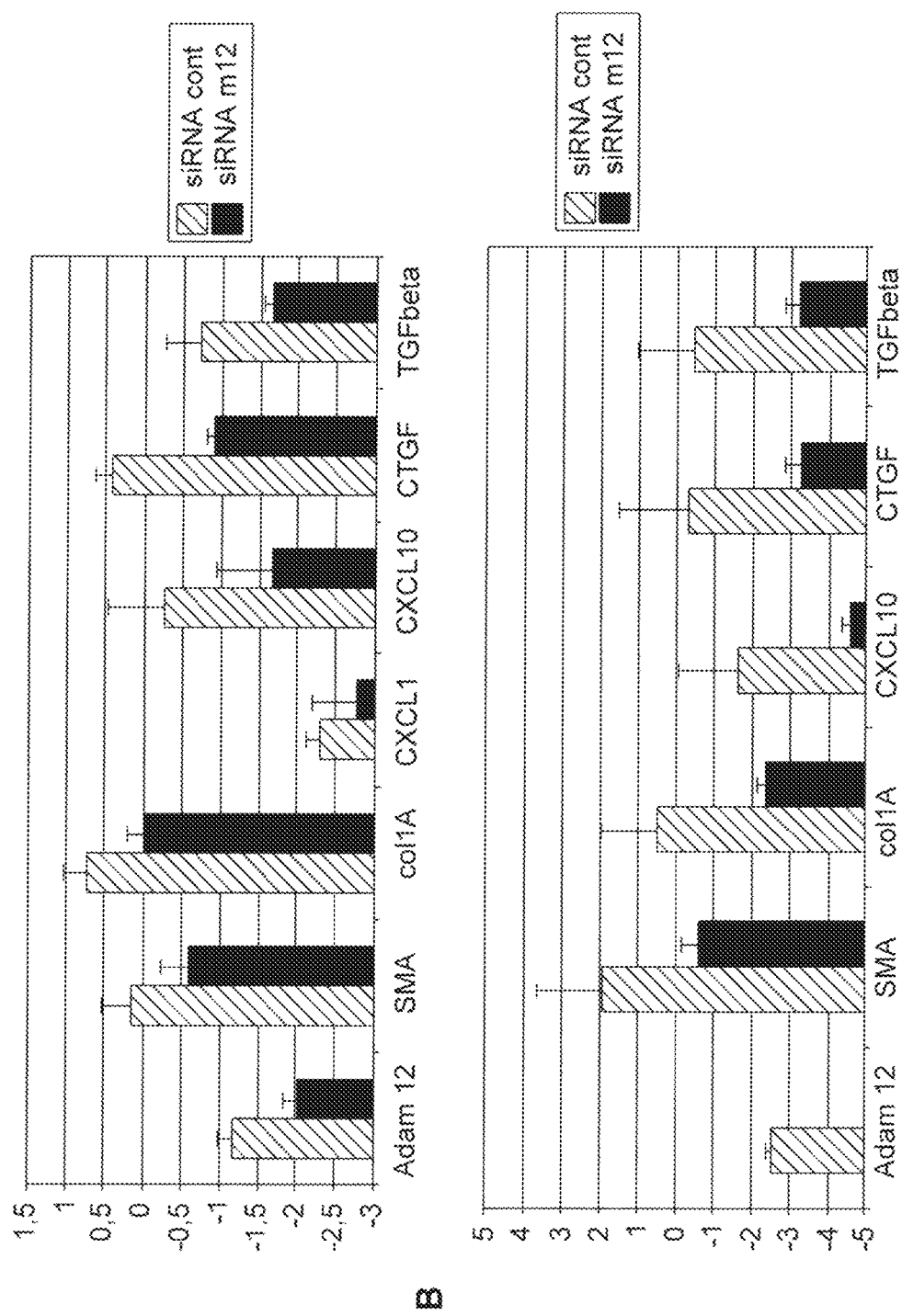
Figure 4:
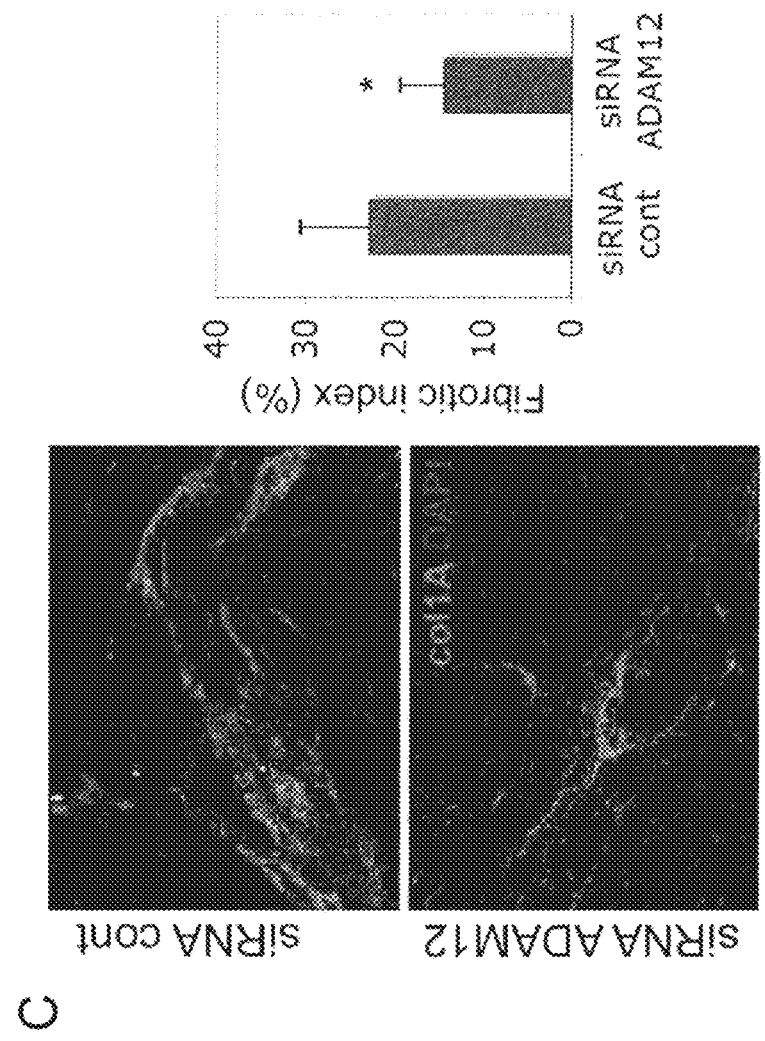

FIG. 4. In vivo knock down of ADAM12 expression by RNA interference during muscle injury and inflammation. Immunofluorescence analysis (A), Gene expression, as measured by quantitative RT-PCR (B); (upper panel: ear skin 6 days after CFA injection; lower panel: muscle 22 days after CX injection), and fibrotic index (C) of inflamed tissues treated with ADAM12 siRNAs at different times as indicated in results. In A, a representative picture of three independent experiments is shown. The fibrotic index was calculated as the % of the injured area occupied by collagen deposit. Error bars, s.d.; *P<0.05, unpaired t-test.

FIG. 5. DNA sequence (5'->3' coding strand) of a polynucleotide which encodes for CRE-IRES-EGFP-flag polypeptide (SEQ ID NO:1). The first 1032 bp code for CRE, the following 581 bp code for IRES, the following 720 bp code for EGFP and the last 24 bp code for flag peptide.

Figure 6:
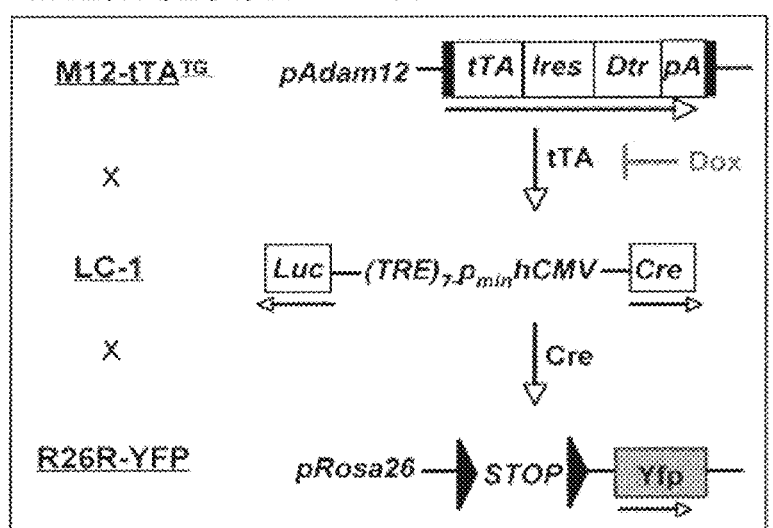

FIG. 6. Strategy for inducible cell fate mapping (A). Sections of injured muscles 3 weeks after CX injection and DTA treatment in M12tTA/LC1/YFP mice were stained as indicated. The number of YFP$^+$ cells and CD45$^+$ cells per field was counted in at least 10 sections of 3 independent experiments (B). Fibrotic index was calculated as the % of the injured area occupied by collagen deposits (C). Error bars, s.d.; *P<0.05, **P<0.005, unpaired t-test.

Figure 7:
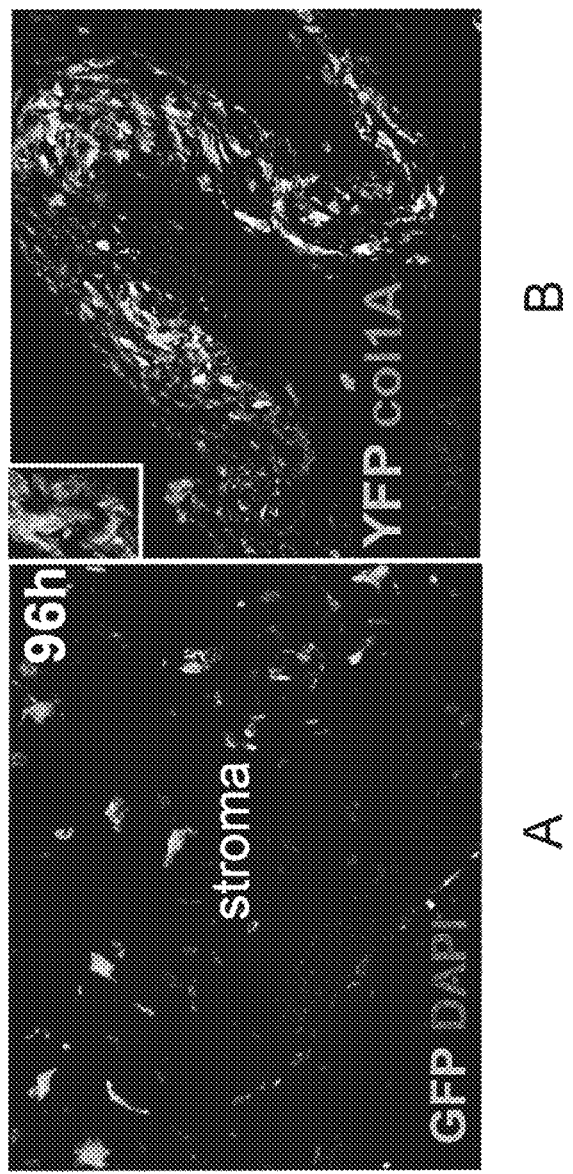

FIG. 7. Sciatic nerve injury was performed in M12-CIG mice (A) and M12tTA/LC1/YFP mice (B). Sections of innervated muscle were stained as indicated in Material & Methods.

DETAILED DESCRIPTION OF THE INVENTION

1. Definitions

"ADAM12" refers to "A Disintegrin And Metalloproteinase 12", also known as meltrin-alpha. There are 2 splice variants of human ADAM12, a transmembrane type (ADAM12-L) and a secreted type (ADAM12-S) (Mino et al, J. Surgical Oncology, 2009, 100: 267-272). In addition to protease activity, ADAM12 possesses cell binding and cell signalling properties. The catalytic domain mediates processing of growth factors and cytokines and has been involved in epidermal growth factor (EGF) and insulin-like growth factor receptor signalling. The disintegrin, cysteine-rich, and EGF-like domains mediate contacts with the extracellular matrix and other cells through interactions with integrins and syndecans. The cytoplasmic domain interacts with intracellular signalling molecules (Jacobsen and Wewer, 2009). Adam12 or Adam12 refers to the gene encoding the ADAM12 protein. In the context of present invention the term "ADAM12" will be used also for referring to the gene. The sequences of the gene and protein are in the prior art, the sequence of the murine gene is available for example from the BAC clone RP23-404F23 from Invitrogen.

"Stromal cells" refer to connective tissue cells of an organ. These are the cells that make up the support structure of biological tissues and support the parenchymal cells. Fibroblasts, immune cells, pericytes, endothelial cells and inflammatory cells are the most common types of stromal cells. In this invention, the term "stromal cells" will be used to refer to non-hematopoietic stromal cells only.

"Activated stromal cells" refer to stromal cells that are activated and proliferate during inflammation and fibrosis.

"Pro-fibrotic stromal cells" refer to subsets of activated stromal cells that promote the formation of fibrosis.

"Diseases related to fibrosis" refer to diseases where fibrosis is an important component of the pathogenesis, such as acute or chronic inflammation, and neuromuscular or neurodegenerative diseases.

"Inflammation-induced fibrosis" relates to fibrosis developing during inflammatory diseases i.e. diseases related to acute or chronic inflammation (caused by tissue injury, pathogen infections or toxic agents) or as a consequence. Fibrosis is the formation of excess fibrous connective tissue during the reparative and reactive process of inflammation. In the context of the present invention, the term "fibrosis" will also be used with the same meaning as "inflammation-induced fibrosis".

"Preventing inflammation-induced fibrosis" relates to a process by which the symptoms of fibrosis are obstructed or delayed.

"Treating inflammation-induced fibrosis" relates to a process by which the symptoms of fibrosis are alleviated or eliminated.

"A pharmaceutically acceptable carrier" relates to a vehicle for containing the ADAM12 inhibitor of the invention that can be administered to a subject without adverse effects. Suitable pharmaceutically acceptable carriers known in the art include, but are not limited to, sterile water, saline, glucose, dextrose or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

"A subject" refers to an animal, for instance a mammal, (e.g. a human).

"EGFP" refers to Enhanced Green Fluorescent Protein.

"CX" refers to cardiotoxin.

"CFA" refers to complete Freud's adjuvant.

2. ADAM12 Inhibitors and Uses Thereof

The present inventors have unexpectedly found that it is advantageous to inhibit ADAM12 in the prevention or treatment of fibrosis.

Accordingly, it is an object of the invention to use compounds or agents that specifically inhibit ADAM12. As used herein, the term "inhibit" when referring to ADAM12 refers to the inhibition of the Adam12 gene expression or to the activity of the ADAM12 protein. In other words, it is meant that the inhibitor contemplated by the present invention has the ability to interfere with the function of the ADAM12 gene or its related proteinic product in such a way as to decrease expression of the ADAM12 gene or to reduce the level or activity of the product of the ADAM12 gene. With respect to the contemplated inhibitors used in accordance with the present invention, the expression "specifically inhibits" refers to a compound or agent that inhibits the expression of the ADAM12 gene or to reduce the level or activity of the product of the ADAM12 gene, but which does not substantially inhibit the expression of another gene or reduce the level or activity of the product of other genes.

Inhibitors which inhibit the activity of a ADAM12 gene include but are not limited to compounds or agents that inhibit transcription of the gene, compounds or agents that inhibit processing of the transcript of the ADAM12 gene, compounds or agents that reduce the stability of the transcript of the ADAM12 gene, and compounds or agents that inhibit translation of the mRNA transcribed from the ADAM12 gene.

Inhibitors which inhibit the biological activity of ADAM12 protein include but are not limited to compounds or agents that inhibit its proteolytic activity, its adhesion activity and/or its cytoplasmic signal transduction activity.

As one skilled in the art will appreciate, inhibitors contemplated by the present invention may be, but are not limited to, an antisense oligonucleotide, a siRNA, a miRNA, a small organic molecule, an enzyme, an antibody, a peptide or a polynucleotide encoding a polypeptide.

For example, small interfering RNA specific for ADAM12 which are commercialized by Invitrogen may be useful within the scope of the present invention, such as Stealth Select RNAi siRNA specific for human ADAM12 (catalog references: 1299003 and 1299001). Small interfering RNAs also include ADAM12 siRNA (h), called sc-41414 provided by Santa Cruz Biotechnology, inc. which is a target-specific 20-25 nt siRNA designed to knock down human gene expression.

By "antibodies" it is meant herein any type of antibody and in particular polyclonal antibodies, monoclonal antibodies, or antibody-like molecules, all which are specific to ADAM12.

The term "monoclonal antibody" encompasses:
monospecific antibodies i.e., molecules wherein the two antigen binding sites (domains formed by the VH regions or by the interaction of the VH and VL regions, and interacting with the immunogen) recognize and bind the same immunogen.
trifunctional antibodies i.e., bispecific molecules as disclosed hereinafter and further having an Fc region (CH2 and CH3 domains) of any origin, particularly of human origin.

The term "antibody-like molecule" refers to a molecule having all or part of the variable heavy and light domains of an antibody, but devoid of the conventional structure of a four-chain antibody, and conserving nevertheless the capacity to interact with and bind an immunogen. In a particular embodiment of the invention, an antibody-like molecule is a fragment of an antibody and in particular comprises the CDR1, CDR2 and CDR3 regions of the VL and/or VH domains of a full length antibody.

The term "antibody-like molecule" encompasses in particular:
scFv, i.e., a VH domain genetically associated (optionally via a linker) to a VL domain, as well as molecules comprising at least one scFv, such as Bis ScFv molecules (two ScFv having same or different antigen binding site(s) linked together (optionally via a linker));
diabody molecules i.e., the heavy chain variable domain derived from a first antibody (a first VH domain (VH1)) connected to the light chain variable domain derived from a second antibody (VL2) on the same polypeptide chain (VH1-VL2) connected by a peptide linker that is too short to allow pairing between the two domains on the same chain, interacting with the heavy chain variable domain of derived from a second antibody (VH2) connected to the light chain variable domain derived from a first antibody (a first VL domain (VL1)) on the same polypeptide chain (VH2-VL1), wherein VL1 and VH1 form a first antigen-binding site and VL2 and VH2 form a second antigen binding site (recognizing and/or binding a similar or a different immunogen from the first binding antigen binding site);

bispecific molecules i.e., molecules in which the two antigen binding sites of a Fab₂ fragment (variable and CH1 domains of light and heavy chains) interact with different immunogens).

trispecific molecules i.e., molecules in which the two antigen binding sites of a Fab₃ fragment (variable and CH1 domains of light and heavy chains) interact with different immunogens);

VHH (VH domain of functional antibodies naturally devoid of light chains) i.e., a VH domain which has the capacity to interact as such with an immunogen, without the presence of a variable light domain (VL).

functional fragments of an antibody or an antibody-like molecule as defined herein, provided that these fragments retain the ability to specifically interact with subset(s) of cells and/or cell surface molecule(s). These fragments include Fv fragments (non-covalent association of the VH and VL domains of the invention) and Fab fragments.

Polyclonal Antibodies are for instance, antibodies provided by Santa Cruz Biotechnology, include ADAM12 (S-18) called sc-16526 or ADAM12 (C-20) called sc-16527, which are affinity purified goat polyclonal antibodies raised against a peptide mapping within an internal region of ADAM12 of human origin or ADAM12 (H-210) called sc-25579, a rabbit polyclonal antibody raised against amino acids 700-909 of ADAM12 of human origin.

Monoclonal antibodies are for example 6E6, 8F8 and 6C10 as described in Kronqvist et al., American Journal of Pathology 161, 5, 2002 and further described in Gilpin et al., J. Biol. Chem., 2002, 160: 1895-1903; Iba et al., Am. J. Pathol., 1999, 154: 1489-1501; Iba et al., J. Cell Biol., 2000, 149:1143-1156.

The inhibitory compounds may be those that are known to affect ADAM12 proteolytic activity including but not limited to: hydroxamate inhibitors, thiol amides which exhibit collagenase inhibition activity (U.S. Pat. No. 4,595,700), N-carboxyalkyl derivatives containing a biphenylethylglycine which inhibit MMP-3, MMP-2 and collagenase (WO 95/29689 by Durette, et al.), lactam derivatives which inhibit matrix metalloproteases, TNF-alpha and aggrecanase (U.S. Pat. No. 6,495,699), tricyclic sulfonamide compounds (U.S. Pat. No. 6,492,422), the compound ONO-4817 from Ono Pharmaceutical Co. Ltd., Osaka, Japan (Mori et al., 2002, Anticancer Res., 22(6C):3985-8) and the collagenase inhibitors GM6001 (trade name Galardin™) and GM1489 (a derivative of GM6001) (U.S. Pat. No. 6,759,432). Specific examples of hydroxamic acid-based metalloprotease inhibitors include the compounds "5A" [NHOHCOCH₂CH(i-Bu)CO-tryptophan-NHMe], "21A" [NHOHCOCH₂CH(i-Bu)CO-tryptophan-NHCHMePh], "39A" [HOOCCH2CH(i-Bu)CO-tryptophan-NHCHMePh], "S1209" [NHOHCOCH2CH(i-Bu)CO-tyrosine-OMeNHMe], UL001 [HSCH₂ CH(CH₂CH(CH₃)₂)CO-Phe-Ala-NH₂] and MP506 (Elastin Products Company, Inc.) (U.S. Pat. Nos. 5,773,438 and 5,892,112). Other compounds, such as KB-R7785, could act as inhibitors of ADAM12 (Akasura M. et al., Nat. Med., 2002, 8, 35.). The matrix metalloprotease inhibitor SB-3CT is also expected to inhibit ADAM12. Additional metalloprotease inhibitors expected to be useful as ADAM12 inhibitory compounds include the various compounds disclosed in U.S. Pat. Nos. 6,500,847; 6,268,379; 5,968,795; 5,892,112; 5,872,152; 4,681,894; 4,943,587 and WO 06/014903. Four selective ADAM12 inhibitors have been described by Oh et al., 2004, Bioorg Med Chem. Lett., 14(24):6071-6074, and called the compounds 5, 11, 14, and 16, having the following structures

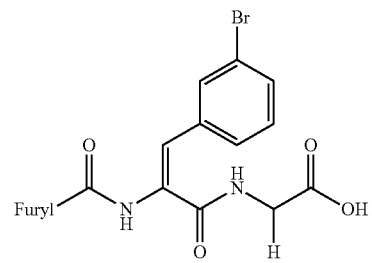
compound 5

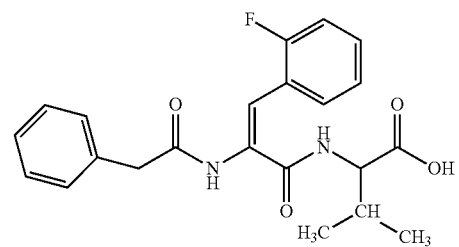
compound 11

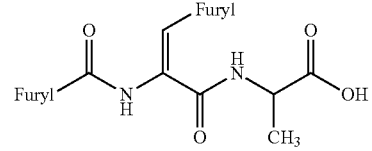
compound 14

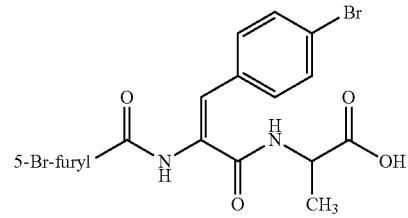
compound 16

Another aspect of the present invention relates to compositions for treating or preventing fibrosis in a subject. The composition of the present invention advantageously comprises at least one inhibitory molecule as defined above. The composition of the invention further comprises a pharmaceutically acceptable carrier.

In a related aspect, the invention provides a method for treating or preventing fibrosis in a subject. The method comprises the step of administering to said subject in need thereof a composition of the invention.

The amount of the inhibitors of the composition of the invention is preferably a therapeutically effective amount. A therapeutically effective amount of the contemplated component is the amount necessary to allow the same to perform its inhibitory role without causing overly negative effects in the subject to which the composition is administered. The exact amount of the inhibitors to be used and the composition to be administered will vary according to factors such as the form of fibrosis being treated, the type and age of the subject to be treated, the mode of administration, as well as the other ingredients in the composition.

The composition of the invention may be given to the subject through various routes of administration. For instance, the composition may be administered in the form of sterile injectable preparations, such as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents. They may be given parenterally, for example intravenously, intramuscularly or sub-cutaneously, by injection, by infusion or per os. Suitable dosages will vary, depending upon factors such as the amount of each of the components in the composition, the desired effect (short or long term), the route of administration, the age and the weight of the subject to be treated. Any other methods well-known in the art may be used for administering the composition of the invention.

As one skilled in the art will understand, the administration of ADAM12 inhibitors during acute and/or chronic inflammation, including infectious or inflammatory diseases is particularly useful to limit the generation of fibrosis and scar tissue. As fibrosis correlates with poor organ recovery, the inhibition of ADAM12 is expected to increase the functionality of the inflamed organ (such as muscle regeneration in the case of muscle inflammation). This will also decrease leukocyte infiltration, aiming at restoring tissue homeostasis and resolving inflammation. Furthermore, since stromal cells represent the reservoir for several infectious agents, such as Chikungunya virus in the muscle, Hepatitis virus in the liver, and Influenza A virus in the lung, the administration of agents that inhibit ADAM12 might be particularly useful to modulate the course of infection of viruses targeting stromal cells, by limiting the expansion of the stromal compartment.

According to the invention, the ADAM12 inhibitor as defined herein is therefore for use in prevention and/or treatment of fibrosis-related diseases as liver cirrhosis, scleroderma, heart and pulmonary fibrosis, atherosclerosis and asthma.

3. Screening Method for Inhibitors of ADAM12 Gene Expression

The invention provides a polynucleotide which consists of a generated bacterial artificial chromosome (BAC) expressing a Cre recombinase and a fluorescent reporter protein: EGFP (Enhanced Green Fluorescent protein) under control of the murine Adam12 gene, and a bacterial strain comprising such polypeptide deposited on Aug. 28, 2009 under No I-4225 at the CNCM.

In another aspect, the invention provides a transgenic mouse which comprises the polynucleotide described above and contained in the bacterial strain of the invention.

Still another object of the invention is to provide a screening method for identifying ADAM12 inhibitors, comprising the steps of:
  inducing an inflammation response at a desired site of the transgenic mouse of the invention,
  applying at the site of inflammation a candidate compound to be tested,
  evaluating expression of the fluorescent reporter EGFP polypeptide; and
  identifying that the expression level of said fluorescent reporter EGFP is inhibited, whereby indicating that the selected compound has the capacity of inhibiting the Adam12 gene expression.

The screening method may further comprise the step of assessing other parameters of inflammation response with and without the compound, as leukocytes (CD45+ cells) infiltration and pro-inflammatory cytokines such as IL1 beta, IL6, TGF beta or TNF alpha.

As one skilled in the art will understand, the candidate compounds will advantageously be tested to confirm that they do not inhibit the expression level of said fluorescent reporter EGFP per se. Therefore, it will be understood that if the tested compound does not inhibit the expression level of said fluorescent reporter EGFP but such expression is yet inhibited according to the screening method of the present invention, one will understand that the selected compound does have the capacity of inhibiting the ADAM12 gene expression.

The screening method of the invention thus allows identification of compounds which interfere directly with the activity of the ADAM12 promoter or which interfere with components of the signal transduction pathway of stromal cells during inflammation upstream from ADAM12.

The screening method of the invention can also be performed with a transgenic mouse which is the heterozygous progeny from crossing ADAM12-CIG mouse with the knock-in Rosa26 mouse (Luche et al., "Faithful activation of an extra-bright red fluorescent protein in "knock-in" Cre-reporter mouse ideally suited for lineage tracing studies". Eur J Immunol. 2007 January; 37(1):43-53). With such a transgenic mouse, the screening method may further comprise a step of evaluating expression of the fluorescent reporter RFP polypeptide. As for EGFP, if the expression level of RFP is decreased with the compound when compared to the control expression level of RFP, one can conclude that the tested compound has the capacity of inhibiting the ADAM12 gene expression, therefore also its proteinic activity.

4. ADAM12 and Use as a Marker for Fibrosis

After transient expression during embryogenesis, ADAM12 is not expressed, or expressed at low levels, in most normal adult tissues under homeostatic conditions. The invention relies on the finding by the inventors that in mouse models for inflammation by skin, muscle or nerve injury, pro-fibrotic stromal cells develop from a pool of progenitor cells re-expressing ADAM12, which are activated at the onset of inflammation and massively proliferate during the first days of inflammation, post injury. These cells produce a large amount of pro-inflammatory cytokines and growth factors and can be detected up to 4 weeks after induction of inflammation. By genetic fate mapping, the inventors observe that inflammation-induced fibrosis is derived from stromal cells re-expressing ADAM12 following tissue injury and inflammation.

Therefore, the present invention further provides the use of ADAM12 as an early marker for inflammation-induced fibrosis.

In a related aspect, there is provided a method for diagnosing fibrosis in a subject. Such a method comprises the step of evaluating if the Adam12 gene is expressed in stromal cells, either by detecting the mRNA level or the protein level. This diagnosis method will indicate that the tested subject suffers or will suffer from fibrosis.

In a related aspect, there is provided a method for diagnosing inflammation-induced fibrosis in a subject comprising:
  detecting the expression of Adam12 gene in stromal cells from a biological sample of said subject,
  relating the expression of Adam12 gene to the presence or the advent of inflammation-induced fibrosis.

Alternatively, is provided a method for diagnosing inflammation-induced fibrosis in a subject, comprising:
  determining the level of Adam12 gene expression in stromal cells from a biological sample of said subject,
  comparing this level with a reference level, whereby an increased level of Adam12 gene expression in said stromal cells with respect to the reference level indicating the presence or the advent of inflammation-induced fibrosis.

According to another embodiment, the present invention is directed to a method for detecting the presence of stromal cells specifically activated upon tissue injury and inflammation and responsible for inflammation-induced fibrosis in a subject comprising:
    detecting the expression of ADAM12 gene in stromal cells from a biological sample of said subject; and
    relating the expression of ADAM12 gene to the presence of stromal cells activated upon tissue injury and inflammation and responsible for inflammation-induced fibrosis.

All the above-mentioned diagnosing and detecting methods of the invention may advantageously further comprise a step of isolating stromal cells, before the step of detection.

According to the invention, the stromal cells which are to be analysed can be from a biopsy. A biopsy according to the invention may be from any organ or tissue. The biopsy is for example a biopsy of muscle, lung, skin, liver or nerve.

The methods of the invention may be carried out in vitro or ex vivo. Indeed and as one skilled in the art will appreciate, the step of detecting the expression of ADAM12 gene may be carried out in vitro or ex vivo.

By "expression of ADAM12 (or Adam12) gene, it is meant an expression which is above the expression of ADAM12 in normal stromal cells under homeostatic conditions, used as a control. Preferably, the normal stromal cells used as control are from the same adult tissue as the one of stromal cells of the biological sample to test. Moreover, according to these embodiments of the invention, the sole detection of the ADAM12 gene over-expression in stromal cells is indicative of the presence of activated stromal cells that could lead to fibrosis. Indeed, as mentioned above, ADAM12 expression in normal stromal cells from adult tissues under homeostatic conditions is very low, ADAM 12 mRNAs and proteins are thus not detectable, or detected at low levels, in normal stromal cells by using standard methods, (e.g. Western blot and immunohistology as detection means for proteins, and Northern blot or in situ hybridization as detection means for RNA), or as sensible or less sensible detection techniques.

In the methods of invention, the expression of ADAM12 gene is determined either by the detection of RNA transcripts from ADAM12 gene or by detection of proteins produced from ADAM mRNAs.

Detection of RNA transcripts can be performed with standard techniques such as Northern blot, in situ hybridization or quantitative RT-PCR.

When the detection of the expression of ADAM12 gene is performed by RNA detection, the "reference level", used during the comparison step, is the level of ADAM12 RNA in normal, healthy stromal cells of the subject to be tested, or of another subject. More preferably, the normal healthy stromal cells used as reference are from the same tissue as the one of stromal cells of the biological sample to test.

Alternatively, when the level of proteins corresponding to ADAM12 RNAs is to be determined, advantageous techniques to be employed are Western blots and in situ immunoassays. The "reference level", used during the comparison step, is the level of ADAM12 protein in normal, healthy stromal cells of the subject to be tested, or of another subject. More preferably, the normal healthy stromal cells used as reference are from the same tissue as the one of stromal cells of the biological sample to test.

By "increased level", it is to be understood that the level is significantly increased, i.e. that the difference between the measured level and the reference level is significant from a statistical point of view, that is the difference is greater that the standard deviation of the measured levels. The difference is thus advantageously greater than the error inherent in the measurement and greater than the variations observed between normal stromal cells. More advantageously, the increased level is at least 3 times higher than the reference level.

The present invention further provides kits for use within the above described diagnostic and detecting methods. Such kits typically comprise two or more components necessary for performing a diagnostic assay. Components may be compounds, reagents, containers and/or equipment. For example, a kit may be designed to detect the level of mRNA encoding an ADAM-12 protein in a biological sample. Such kit generally comprises at least one oligonucleotide probe or primer that hybridizes to a polynucleotide encoding an ADAM-12 protein. Such an oligonucleotide may be used, for example, within a PCR or hybridization assay. Additional components that may be present within such kits include a second oligonucleotide and/or a diagnostic reagent or container to facilitate the detection of a polynucleotide encoding an ADAM-12 protein. Such kits may also, or alternatively, contain a monoclonal antibody or fragment thereof that specifically binds to an ADAM-12 protein. Such antibodies or fragments may be provided attached to a support material, as known to one skilled in the art. One container within such a kit may also contain a detection reagent that contains a reporter group suitable for direct or indirect detection of antibody binding. One or more additional containers may enclose elements, such as reagents or buffers, to be used in the assay.

5. Method for Killing ADAM12-Expressing Stromal Cells

In another aspect, the present invention provides the use of ADAM12 as a target to specifically kill stromal cells activated during inflammation-induced fibrosis.

This aspect of the invention relies on the finding by the inventors that in mouse models for muscle injury and inflammation, the genetic ablation of ADAM12-expressing cells decreases inflammation and fibrosis in chronic lesions.

Therefore, the present invention provides a cytotoxic compound for use to kill ADAM12-expressing cells. Therefore the present invention provides a cytotoxic compound for use to prevent or treat inflammation-induced fibrosis.

A cytotoxic compound of the invention may comprise a targeting molecule and a cytotoxic molecule and is able to specifically kill ADAM12-expressing stromal cells.

The targeting molecule specifically recognizes ADAM12-expressing cells by binding to ADAM12 protein or ADAM12 mRNA present in or at the surface of the cell. The targeting molecule is, for example, an antibody raised specifically against ADAM12 protein or any part thereof, or a small interfering RNA specific for ADAM12. Examples of antibodies and small interfering RNA specific for ADAM12 are described above.

The cytotoxic molecule is, for example, a toxin, such as Pseudomonas exotoxin (Wolf et al., Int J Med Microbiol., 2009 March; 299(3):161-76. Epub 2008 Oct. 23), deglycosilated ricin A-chain (dgA) (Schnell et al., Ann Oncol., 2003 May; 14(5):729-360) or the cytotoxic drug maytansinoid 1 (DM1) (Kovtun et al., Cancer Res. 2010 Mar. 15; 70(6): 2528-37. Epub 2010 Mar. 2).

The targeting molecule and the cytotoxic molecule are associated in the cytotoxic compound by chemical coupling.

The invention is also directed to the cytotoxic compound as defined herein for use in the prevention and/or the treatment of fibrosis.

The invention also relates to a cytotoxic compound as defined herein, for use in combination with another anti-inflammatory drug to prevent or treat fibrosis.

As ADAM12 is involved in other pathologies than fibrosis-related diseases, such as arthrosis, cardiac hypertrophy, neurodegenerative diseases, neuromuscular diseases and cancer, the cytotoxic compound as defined herein can be used for preventing or treating these diseases.

The present invention will be more readily understood by referring to the following examples. These examples are illustrative of the wide range of applicability of the present invention and are not intended to limit its scope. Modifications and variations can be made therein without departing from the spirit and scope of the invention. Although any methods and materials similar or equivalent to those described herein can be used in the practice for testing of the present invention, the preferred methods and materials are described. Several experiences have been repeated, with some changes. All references cited in the present application are incorporated by reference.

EXAMPLES

The present inventors now present a role for ADAM12 in the inflammation process such as inflammation resulting from tissue injury, and more particularly in inflammation-induced fibrosis and generation of pro-fibrotic cells. It is shown that ADAM12 expression increases upon skin, muscle and nerve injury (tissue injury is a way to induce inflammation) as activated stromal cells start to expand, before being down regulated in later fibrotic lesions. These cells produce a large amount of pro-inflammatory cytokines and/or growth factors. Genetic fate mapping indicate that most inflammation-induced fibrosis is progeny of ADAM12-expressing cells that massively proliferate in the first days after induction of inflammation caused by tissue injury. In vivo treatment with ADAM12 specific small interfering RNA in mice leads to a reduction of inflammation-induced fibrosis. It is also shown that specific ablation of ADAM12-expressing cells generated post injury is sufficient to mitigate the pro-fibrotic process. Accumulation of alpha-SMA+ pro-fibrotic cells, and collagen are significantly reduced. In accordance with a role for stromal cells in the recruitment of leucocytes, the inhibition of ADAM12 or the ablation of ADAM12+ cells lead locally to a decrease in the recruitment of CD45+ cells in the inflamed tissues. The inventors' results demonstrate that stromal cells and the immune system communicate through a cellular crosstalk to generate an effective immune response. Hence the overactivation of stromal cells, through a pathway involving ADAM12, disrupts homeostasis by maintaining the recruitment of immune cells.

These results indicate that ADAM12 plays an essential role in the development of inflammation-induced fibrosis, and suggest that the overactivation of stromal cells, through a pathway involving ADAM12, might be involved in maintaining the recruitment of immune cells.

Material & Methods

Mice. Generation of ADAM12-CIG mice (M12-CIG). The coding sequence for CRE-IRES-EGFP-flag (FIG. 5—SEQ ID NO:1), including the stop codon and a polyA sequence, was generated by overlap PCR and inserted into exon 1 of Adam12 mouse gene in place of the endogenous ATG translation start codon, on a 200-kb Bacterial Artificial Chromosome (BAC) (clone RP23-404F23 from Invitrogen) carrying at least 70 kb, preferably 80 kb of sequence upstream of the Adam12 translation start site. Generation of ADAM12-tTA-ires-Dtr$^{TG}$ mice (M12-tTA): the coding sequence for tTA-ires-Dtr, including a poly A sequence, was generated by overlap PCR and inserted into exon 1 of Adam12 in place of the endogenous ATG translation start codon, on the same 200 kb BAC as described above.

Growth Conditions And Viability Of Bacteria BAC-M12-CIG

1. If starting from a frozen stock of bacteria, streak a few crystals onto plates LB containing 12.5 µg/ml chloramphenicol
2. Incubate O/N at 37° C.
3. Perform direct colony PCR on 4 colonies with primers specific for the gene cre, as described:
  A. Pick Colonies:
  Pick a colony with a 200 µl tip on a pipette
  Agitate it in 5 ml LB miniculture+12.5 µg/ml Chloramphenicol
  Wash the tip in 100 µl water
  B. Perform PCR with 5 µl of Water in 25 µl Reactions:
  H$_2$O to 25 µl
  Buffer 10×2.5 µl
  MgCl$_2$ 50 mM 0.75 µl
  dNTPs 10 mM 0.5 µl
  Regular Taq 0.4 µl
  Primers 25 mM 0.5 µl each
  Substrate (water+colony) 5 µl
  PCR Program:
  1. 96° C. 5 min
  2. 96° C. 30 sec
  3. 58° C. 30 sec
  4. 72° C. for 1 min
  5. Repeat steps 2-4 34×
  6. 72° C. 7 min
  7. 4° C. for ever
  Primers Sequence for Detection of Cre:

```
119 sequence (5'-3'):
                                    (SEQ ID NO: 2)
TAA AGA TAT CTC ACG TAC TGA CGG TG 120 sequence (5'-3'):
                                    (SEQ ID NO: 3)
TCT CTG ACC AGA GTC ATC CTT AGC
```

C. Load PCR Reactions onto 1% Normal Agarose. Positive Band 0.25 kb
4. Grow the positive minicultures O/N in 3 ml LB+12.5 µg/ml chloramphenicol
5. The next day, freeze aliquots of positive minicultures and/or put 1 ml in 500 ml LB+Chloramphenicol (grow again O/N at 37° C. with agitation) for preparation of BAC DNA.

After modification of the ADAM12 BAC in vitro by homologous recombination, M12-CIG and M12-tTA BACs containing the inserted sequences were purified and injected into fertilized eggs implanted into foster mothers by homologous recombination as previously described (Sparwasser et al., "General method for the modification of different BAC types and the rapid generation of BAC transgenic mice". Genesis. 2004 January; 38(1):39-50).

Cell fate mapping experiments were performed by crossing M12-CIG mice with the knock-in Rosa26+/FI RFP mice (Luche et al., "Faithful activation of an extra-bright red fluorescent protein in "knock-in" Cre-reporter mice ideally suited for lineage tracing studies". Eur J Immunol. 2007 January; 37(1):43-53). For inducible cell fate mapping, M12-tTA$^{TG}$ mice were crossed with doxycycline-dependent LC1-Cre mice (Schonig, K., Schwenk, F., Rajewsky, K. & Bujard, H. Stringent doxycycline dependent control of CRE recombinase in vivo. *Nucleic Acids Res.* 30, e134., 2002) and then further crossed with Rosa26$^{+/loxP-YFP}$ mice (Srinivas et al. Cre reporter strains produced by targeted insertion of EYFP and ECFP into the ROSA26 locus. *BMC Dev Biol* 1, 4, 2001).

All mice were kept in specific pathogen-free conditions and animal experiments were approved by the committee on animal experimentation of the Institut Pasteur and by the French Ministry of Agriculture.

Mice Treatment. Mice were anaesthetized with 100 µl of Xylazine/Ketamine. To induce ear skin inflammation, ears were injected intradermally with 25 µl of Complete Freud Adjuvant (CFA). To induce muscle inflammation, Tibialis Anterior (TA) muscles were injected locally with 50 µl of 10 µM cardiotoxin (CX) in PBS. To perform nerve crush injury, the sciatic nerve in the thigh was exposed and slightly crushed with forceps.

At different time points after treatment, the inflamed ears (including the muscle base), the cardiotoxin-treated TA muscles and the injured nerve were removed and processed for histology.

M12tTA/LCl/YFP triple transgenic mice were treated with doxycycline (Sigma Aldrich) at 1 mg/ml in drinking water containing 5% Sucrose to stop fate-mapping labelling.

To delete ADAM12$^+$ cells, M12tTA/LCl/YFP mice were injected with DTA (Diphtheria toxin subunit A) at days 4, 7 and 10 after CX injection, and tissues were collected after 3 weeks.

Cells Isolation and FACS. To isolate GFP cells, inflamed muscles and ears from adult mice were removed and washed with PBS (Ca/Mg free), cut into 1 mm pieces and incubated at 37° C. for 30 min in a digestion medium composed of DMEM (Gibco) containing 1 mg/ml collagenase D (Roche), blendzyme III (Roche) and 1 U/ml DNase 1 (Invitrogen). After 30 minutes, tissues were washed with DMEM 10% FCS and the supernatant was collected. Remaining undigested tissues were subjected to 1 or 2 additional cycles of 30 min digestion, washed, mixed with the collected supernatants and pressed through a 100-µm mesh.

Knock Down of ADAM12 by RNAi. To induce the knock down of ADAM12 gene expression, inflamed tissues were treated with Stealth RNAi small interfering RNA (siRNAs) targeting mouse ADAM12 (purchased as MSS273021 from Invitrogen). Effective ADAM12 knock down was first validated in vitro by screening three pre-designed ADAM12 specific siRNAs in mammalian stromal cell lines (OP9). The siRNA inducing the best ADAM12 knock down in vitro was chosen for subsequent in vivo studies. In vivo knock down in tissues was performed following manufacturer's recommended procedure. Briefly, in vivo quality purified siRNAs were mixed with Invivofectamine™ (Invitrogen) to obtain a final concentration of 20 mg/ml RNAi duplex. The lipid complex was then diluted with 10 ml 5% glucose and concentrated using Amicon Ultra-15 Centrifugal Device™ with Ultracel-50 Membrane™ (Millipore). The retentate containing the Invivofectamine-RNAi complex was collected, resuspended in 5% glucose solution and sterilized by filtering through a 0.22 µm filter prior to injection. siRNAs were delivered locally by injecting 15 µl of 20 mg/ml siRNA solution in the ear skin at day 1 and day 3 after CFA injection; and in the tibialis anterior muscle at days 2, 7, and 12, or at days 2, 7, 12, and 17 after cardiotoxin-induced muscle inflammation through Injection of cardiotoxin. CFA-inflamed ears treated with siRNAs were collected at day 6 and cardiotoxin-inflamed muscles were collected after three weeks around day 22. Control experiments were performed by injecting scrambled (cont) siRNAs duplex with similar GC content.

Gene Expression Analysis. To obtain RNA for gene expression analysis by real time RT-PCR, 500-5000 cells were directly FACS-sorted into vials containing RLT buffer (Qiagen) supplemented with β-mercaptoethanol (see part "Cells isolation and FACS" for detailed protocol), and total RNA was extracted using RNeasy Micro Kit™ (Qiagen). The quality of total RNA was assessed using the 2100 Bioanalyzer system (Agilent Technologies). 250-500 pg of high quality total RNA was subjected to one linear mRNA amplification cycle using the MessageBooster Kit for qRT-PCR (Epicentre Biotechnologies). 50-100 ng of amplified mRNA was transcribed into cDNA using Superscript III reverse transcriptase (Invitrogen).

In RNAi knock down experiments of inflamed organs, 2 mm$^2$ of tissue were snapped-freezed and total RNA was extracted with Rneasy Kit™ (Qiagen). The quality of total RNA was assessed using the 2100 Bioanalyzer™ system (Agilent Technologies). When necessary, 250-500 pg of high quality total RNA was subjected to one linear mRNA amplification cycle using the MessageBooster Kit™ for qRT-PCR (Epicentre Biotechnologies). 50-100 ng of amplified mRNA were then converted to cDNA using Superscript III™ (Invitrogen).

All procedures were performed according to the manufacturer's protocols. The expression of genes of interest was measured by quantitative real time PCR which was performed using RT$^2$ qPCR Primer sets and RT$^2$ SYBR-Green master mix (SABiosciences) on a PTC-200 thermocycler equipped with a Chromo4 detector (Bio-Rad Laboratories). Data was analyzed using Opticon Monitor Software (Bio-Rad Laboratories). CT values were normalized to the mean CT values obtained for the two house keeping genes Hsp90 and Gapdh. All primers used in qRT-PCR were purchased from SABiosciences.

Immunofluorescence Histology. Tissue processing and immunofluorescence protocol have been described previously (Peduto et al., 2009). Briefly, tissues were fixed O/N at 4° C. in 4% paraformaldehyde (Sigma), then washed O/N in PBS, incubated for 2-4 hours in a solution of 30% sucrose (Sigma) until the samples sank, embedded in OCT compound 4583™ (Sakura Finetek), frozen in a bath of isopentane cooled with liquid nitrogen and stocked at −80° C. Frozen blocks were cut at 8 µm thickness and sections were processed for staining: after blocking with 10% bovine serum in PBS containing 1% Triton (PBS-XG) for 1 hour at room temperature, slides were incubated with primary polyclonal Ab in PBS-XG overnight at 4° C., washed 3 times 5 min with PBS-XG, incubated with secondary conjugated polyclonal Ab or streptavidin for 1 hour at room temperature, washed once, incubated with 4'6-diamidino-2-phenylindole-2HCl (DAPI) (Sigma) 5 min at room temperature, washed 3 times 5 min and mounted with Fluoromount-G™ (Southern Biotechnology associates). Slides were examined under an AxioImager M1™ fluorescence microscope (Zeiss) equipped with a CCD camera and images were processed with AxioVision™ software (Zeiss).

Antibodies. Purchased from BD Biosciences: biotynilated anti-CD45.2.

Purchased from Sigma: Cy3-conjugated anti-αSMA (1A4) and streptavidin.

Purchased from Serotec: rabbit anti-mouse collagen 1A antibodies.

Purchased from Invitrogen: purified rabbit anti-GFP (A-11122), FITC-conjugated anti-rabbit polyclonal antibodies, Alexa Fluor 488 or 647-conjugated anti-rabbit IgG (H+L).

Purchased from Andrew Farr (University of Washington, Seattle, Wash. Seattle): anti-gp38 culture supernatant.

Purchased from Jackson Immunoresearch: Cy3 conjugated anti-syrian hamster.

Purchased from Abcam: chicken anti-GFP polyclonal antibodies.

Chemicals. CFA was purchased from Sigma. Cardiotoxin was purchased from Latoxan (Valence, France).

Results

Generation of BAC Transgenic Mice ADAM12 CRE-IRES-EGFP

Figure 1:
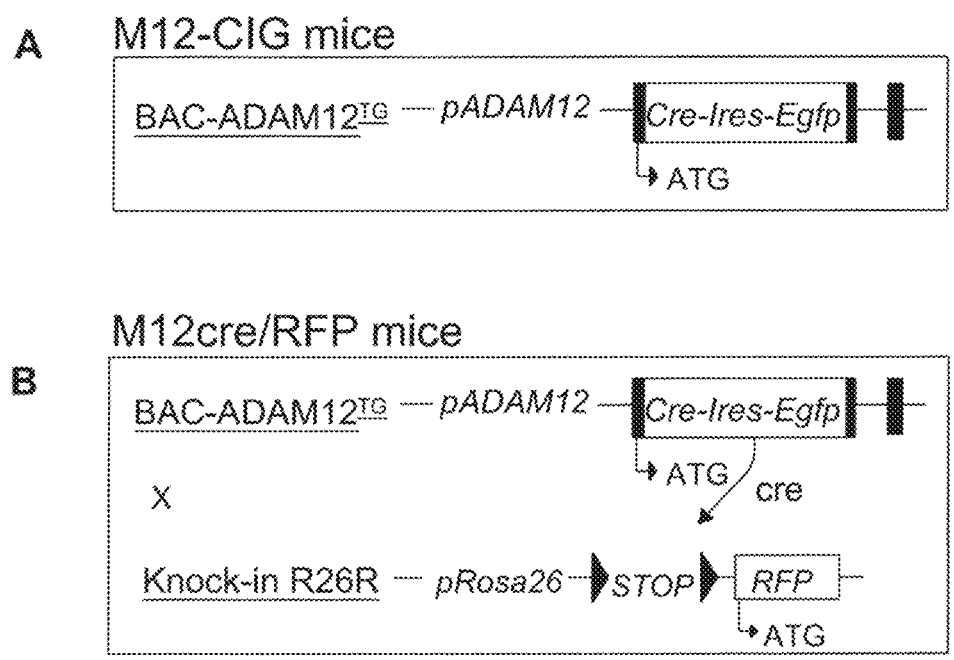
FIG. 1. Generation of the BAC-transgenic mice ADAM12-cre-ires-egfp (A) and cell fate mapping strategy (B).

ADAM12 has been previously described to be overexpressed in a number of pathologies, including muscle injury (Borneman et al., "Analysis for transcript expression of meltrin alpha in normal, regenerating, and denervated rat muscle". *J Muscle Res Cell Motil.*, 2000, 21:475-480,) and cancer (Peduto et al., "ADAM12 is highly expressed in carcinoma-associated stroma and is required for mouse prostate tumor progression". Oncogene. 2006 Aug. 31; 25(39):5462-6). To get a better insight into the development of ADAM12-expressing cells, the inventors generated bacterial artificial chromosomes (BAC) transgenic mice expressing Cre recombinase and the fluorescent reporter EGFP under control of the Adam12 gene (Adam12-Cre-Ires-EGFPTG mice, referred thereafter as m12-CIG) (FIG. 1A). Given the large size of BACs, most if not all regulatory sequences are present in order to maximize chances to direct faithful and tissue-specific expression of the transgene. To allow visualization of ADAM12 expression at the same time than cell fate mapping of these cells, M12-CIG mice were bred to R26R red fluorescent reporter mice, which express RFP under control of the ubiquitously active gene Rosa26 after a LoxP-flanked STOP cassette is excised by Cre (Luche et al., "Faithful activation of an extra-bright red fluorescent protein in "knock-in" Cre-reporter mice ideally suited for lineage tracing studies". Eur J Immunol. 2007 January; 37(1):43-53). In these mice (referred thereafter as M12cre/RFP mice, FIG. 1B), any cell that had expressed ADAM12 will permanently be labelled with RFP.

ADAM12 Labels Stromal Cells Arising During CFA-Induced Skin Inflammation

Figure 2:
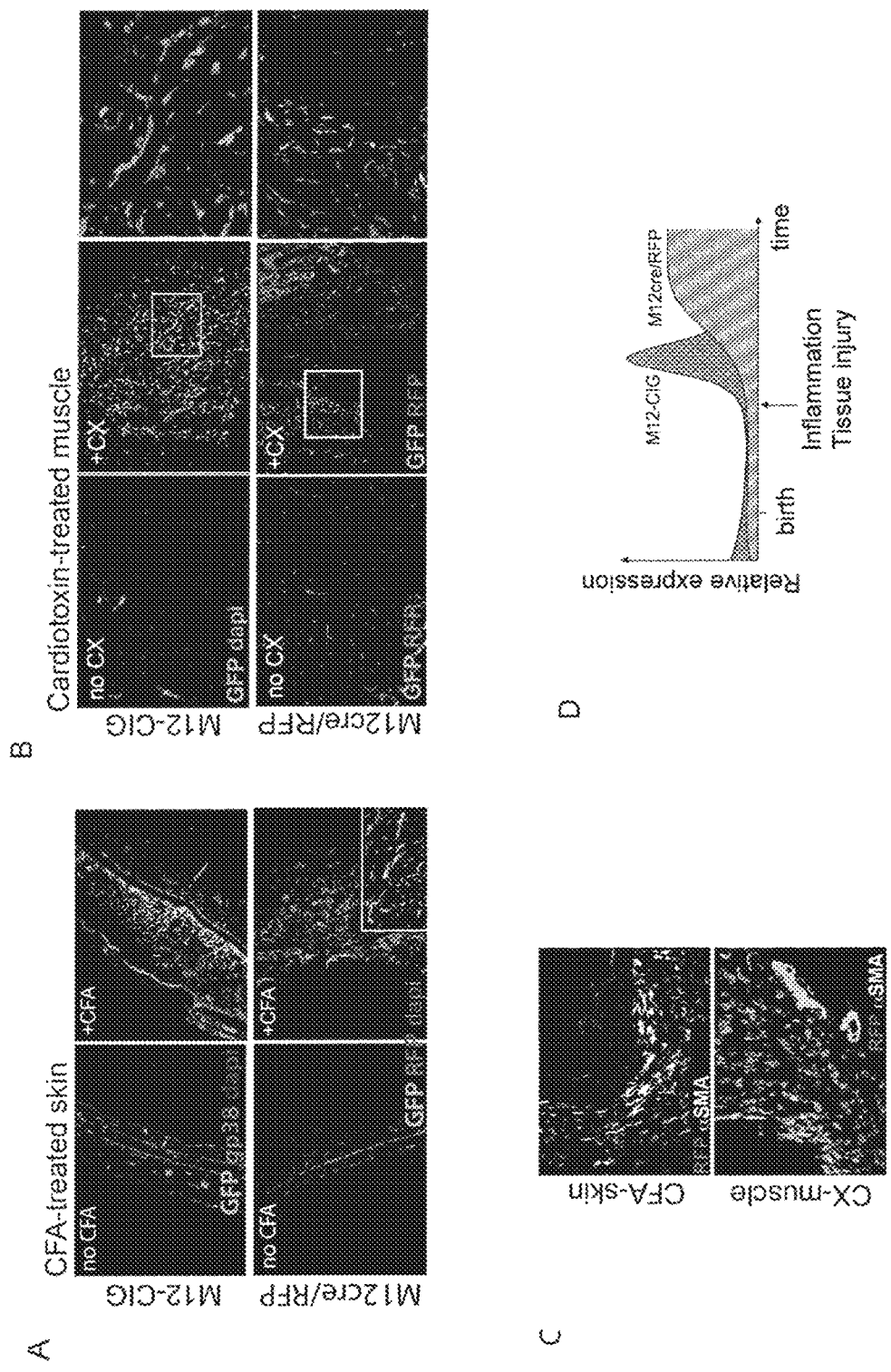
FIG. 2. ADAM12 expression (M12-CIG) and cell fate mapping of ADAM12-expressing cells (M12cre/RFP) in CFA-induced skin inflammation (A) and cardiotoxin-induced muscle inflammation (B) at 4 days for ADAM12 expression and 15 days for fate mapping experiment. Co-staining with alpha-smooth muscle actin antibodies after 30 days (C). In (D), schematic description of ADAM12 expression (first peak) and fate mapping of ADAM12+ cells (second peak).

ADAM12 is not expressed or expressed at very low levels in normal adult tissues, such as muscle, skin or nerve under homeostatic conditions. To determine whether ADAM12 may be involved in tissue injury and inflammation, the inventors induced skin inflammation by injecting Complete Freud Adjuvant (CFA) in the ear. The inventors observed the generation of an important population of ADAM12+ cells starting as soon as 24 h after injection of CFA. These cells expanded rapidly until 96 h and were predominantly found surrounding the muscle fibers at the base of the ear (FIG. 2A, top panel; the green staining observed in the left panel—ear without CFA—is autofluorescence of the tissue and is used to better delineate the ear). To perform lineage tracing of ADAM12-expressing cells during inflammation, M12-CIG mice were crossed with Rosa26+/FL RFP. In the resulting M12cre/RFP mice, the inventors observed that the large population of lymphoid gp38+ SMA+ stroma expanding after CFA injection, which the inventors previously characterized as being essential for leucocyte recruitment and survival (Peduto et al., "Inflammation recapitulates the ontogeny of lymphoid stromal cells." J Immunol. 2009 May 1; 182(9):5789-99), was RFP and therefore was derived from precursor cells that had expressed ADAM12 (FIG. 2A, lower panel and FIG. 2C, top panel). GFP+ expression decreased rapidly after 4 days, however could still be detected in few RFP+ cells 2 weeks after CFA-inflammation (FIG. 2A, lower panel).

Cell Fate Mapping of ADAM12-Expressing Cells During Muscle Inflammation

After injury, muscle healing occurs through different phases, including muscle degeneration and inflammation, muscle regeneration, and development of fibrosis. The inventors induced muscle injury and regeneration in m12-CIG mice by injecting cardiotoxin (CX) in the Tibialis Anterior (TA) muscle. After a first phase of muscle damage induced by the toxin and local inflammation, muscle stem cells become activated to regenerate the muscle fibers in 2-3 weeks. A similar ADAM12 expression than in skin inflammation was observed. GFP+ cells were rapidly detected in stromal cells filling the damaged and highly infiltrated regions of the muscle, with the strongest expression at day 4-5 after cardiotoxin injection (FIG. 2B, top panel), which corresponds to the inflammatory phase (with high leucocytes infiltration). To allow visualization of ADAM12 expression at the same time than cell fate mapping of their progeny, further experiments were performed in the M12cre/RFP mouse. After the first wave of high ADAM12 expression, GFP+ cells decreased notably but were still detected in the stroma of regenerating muscle 15 days after CX injection (FIG. 2B, lower panel). At the same time than the number of GFP+ cells decrease in the damaged regions, a massive increase of fate-mapped RFP+ SMA+ cells was observed. After 3-4 weeks, the inventors observed that more than 50% of fibrosis (from 50% to 80%, as defined by myofibroblasts staining with alpha-SMA antibodies) was RFP, and therefore was progeny of precursors cells that had expressed ADAM12 (FIG. 2B, lower panel; and FIG. 2C lower panel).

Altogether, these results show that ADAM12 is transiently overexpressed following muscle and skin injuries and inflammation. The progeny of ADAM12+ cells (RFP+ cells) increase thereafter (FIG. 2D), making ADAM12 a specific marker for fibrosis ADAM12-Expressing Cells Express Pro-Inflammatory Genes During inflammation, tissue-resident cells play a pivotal role by providing inflammatory signals and growth factors. To get a better understanding of the nature of ADAM12-expressing cells generated upon tissue injury and inflammation, CD45-GFP+ and CD45-GFP− cells were FACS-sorted at days 2-4 after cardiotoxin injection. Total RNA was extracted from these subsets of stromal cells, and transcripts' expression was measured by using quantitative reverse transcriptase (qRT)-PCR.

The inventors observed that, compared to GFP− cells, GFP+ cells up-regulated transcripts for IL1 beta, IL-6, and TNF-alpha, all with known proinflammatory functions; TGF beta, a master gene involved in myofibroblast differentiation; as well as CXCL1 and CXCL10, both involved in leucocytes recruitment (FIG. 3A). In addition, they expressed high levels of pleiotropic growth factors CTGF (connective tissue growth factor), IGF1 and FGF1, and of col1A responsible for the synthesis of type I collagen deposited in the extracellular matrix (FIG. 3B).

ADAM12 Knock Down In Vivo by RNA Interference Decreases Inflammation-Induced Fibrosis To determine whether ADAM12 is directly involved in the generation of fibrotic lesions occurring during inflammation, ADAM12 was knocked down in vivo in inflamed tissues by injecting ADAM12-specific siRNA (following a protocol described in Materials & Methods).

Ear skin or Tibialis Anterior muscles were first injected respectively with CFA and cardiotoxin to induce inflammation, and a solution of siRNA/invivofectamine specially formulated for in vivo delivery of siRNAs was injected locally at days 1 and 3 after CFA injection, and at days 2/7/12 or 2/7/12/17 after CX injection. Control tissues were injected with scrambled siRNAs with similar GC content. The tissues were collected at day 6 for CFA-ear and at day 22 for CX-muscle, and processed for histology or snapped-freezed for subsequent RNA extraction. The inventors observed that the accumulation of stromal extracellular matrix (as detected by staining with ERTR7 antibodies) was decreased locally in the tissues treated with ADAM12 siRNAs compared with tissues treated with scrambled siRNA (FIG. 4A). The lymphoid stromal cells expanding during inflammation were previously characterized as expressing gp38 (Peduto et al., 2009). The inventors also observed a decrease in the population of gp38+ lymphoid stromal cells, and in accordance with a role for gp38+ cells in recruiting leucocytes, a decreased number of CD45+ cells were locally infiltrating the tissues (FIG. 4A, a representative picture of three independent experiments is shown). In agreement with the histology results, quantitative RT-PCR indicated a decrease in SMA expression (expressed by myofibroblasts mainly responsible for fibrosis expansion); as well as a decrease in transcripts coding for type I collagen (col1A), CXCL1 and CXCL10; and CTGF and TGF beta, which represent essential players of myofibroblast development (FIG. 4B). The detected decrease in CXCL1 and CXCL10 in total tissue may be involved in the observed decrease in leucocyte recruitment. The decrease was more pronounced in the muscle tissue after 22 days, even though it was already evident in the ear after 6 days. The qRTPCR results represent 3 independent experiments.

The inventors observed that the fibrotic index (as determined by accumulation of collagen measured by staining with col1A antibodies) was decreased locally in muscles treated with ADAM12 siRNAs compared to muscles treated with scrambled siRNA (FIG. 4C).

Ablation of ADAM12-Expressing Cells Decreases Inflammation and Fibrosis

M12tTA/LC1/YFP mice were generated that express tTA and the diphteria toxin receptor (DTR) under control of the Adam12 locus on a BAC, as well as the tTA-controlled expression of Cre (LC-1) and the reporter Rosa26$^{+/loxP\text{-}EYFP}$ locus (FIG. 6A). In these mice, the permanent YFP-labeling of the progeny of ADAM12$^+$ cells is controlled in time by the administration of doxycycline (dox), which blocks the tTA-mediated labeling cascade, allowing for a time-controlled fate mapping of ADAM12$^+$ cells. To formally demonstrate that cells overexpressing ADAM12 upon tissue injury and their progeny are required for the fibrotic process, M12tTA/LC1/YFP mice were injected with diphtheria toxin subunit A (DTA) 4, 7 and 10 days after cardiotoxin injection to induce the ablation of ADAM12$^+$ cells. As expected, injection of DTA induced a marked reduction in the generation of YFP$^+$ cells (FIG. 6B). Consistent with the pro-inflammatory nature of ADAM12$^+$ cells (FIG. 3), leucocytes infiltration was significantly decreased upon DTA treatment (FIG. 6B, CD45+ cells). As a consequence of the loss in ADAM12$^+$ cells-derived pro-fibrotic stroma, collagen accumulation was reduced in injured muscles (FIG. 6C).

Nerve Injury Triggers the Generation of ADAM12+ Cells

Damage to a nerve triggers degeneration of the axon distal to the injury, as well as activation of stromal and inflammatory cells (Chen, Z. L., Yu, W. M. & Strickland, S. Peripheral regeneration. *Annu Rev Neurosci.*, 2007, 30, 209-233). Sciatic nerve injury alone induced, in the innervated muscle, the transient development of GFP$^+$ cells in the first days post-injury (FIG. 7A left panel), and of their cellular progeny that co-localized with collagen deposits, 2-3 weeks post-injury (FIG. 7A right panel)

The invention claimed is:

1. A method of treating inflammation-induced fibrosis in the skin or muscle of a subject, comprising administering to said subject a composition comprising a cytotoxic compound, wherein the cytotoxic compound comprises a cytotoxic molecule which is a toxin and an antibody targeting ADAM12 (A Disintegrin and Metalloproteinase 12) protein, wherein the antibody is coupled to the cytotoxic molecule.

2. The method of claim 1, wherein the cytotoxic compound affects or inhibits ADAM12 protein activity.

3. The method of claim 1, wherein the composition further comprises a pharmaceutically acceptable carrier.

4. The method of claim 1, wherein the toxin is selected from the group consisting of pseudomonas exotoxin, deglycosilated ricin A-chain (dgA) and maytansinoid 1 (DM1).

5. The method of claim 1, wherein the antibody is a polyclonal antibody or a monoclonal antibody.

6. The method of claim 1, wherein the inflammation-induced fibrosis is triggered by a nerve injury.

* * * * *

SEQUENCE LISTING

<160> NUMBER OF SEQ ID NOS: 3

<210> SEQ ID NO 1
<211> LENGTH: 2369
<212> TYPE: DNA
<213> ORGANISM: Artificial Sequence
<220> FEATURE:
<223> OTHER INFORMATION: Coding sequence for CRE-IRES-EGFP-flag

<400> SEQUENCE: 1

```
atgtccaatt tactgaccgt acaccaaaat ttgcctgcat taccggtcga tgcaacgagt      60
gatgaggttc gcaagaacct gatggacatg ttcagggatc gccaggcgtt ttctgagcat     120
acctggaaaa tgcttctgtc cgtttgccgg tcgtgggcgg catggtgcaa gttgaataac     180
cggaaatggt ttcccgcaga acctgaagat gttcgcgatt atcttctata tcttcaggcg     240
cgcggtctgg cagtaaaaac tatccagcaa catttgggcc agctaaacat gcttcatcgt     300
cggtccgggc tgccacgacc aagtgacagc aatgctgttt cactggttat gcggcggatc     360
cgaaaagaaa acgttgatgc cggtgaacgt gcaaaacagg ctctagcgtt cgaacgcact     420
gatttcgacc aggttcgttc actcatggaa aatagcgatc gctgccagga tatacgtaat     480
ctggcatttc tggggattgc ttataacacc ctgttacgta tagccgaaat tgccaggatc     540
agggttaaag atatctcacg tactgacggt gggagaatgt taatccatat tggcagaacg     600
```

```
aaaacgctgg ttagcaccgc aggtgtagag aaggcactta gcctgggggt aactaaactg      660
gtcgagcgat ggatttccgt ctctggtgta gctgatgatc cgaataacta cctgttttgc      720
cgggtcagaa aaatggtgt tgccgcgcca tctgccacca gccagctatc aactcgcgcc      780
ctggaaggga ttttgaagc aactcatcga ttgatttacg gcgctaagga tgactctggt      840
cagagatacc tggcctggtc tggacacagt gcccgtgtcg gagccgcgcg agatatggcc      900
cgcgctggag tttcaatacc ggagatcatg caagctggtg gctggaccaa tgtaaatatt      960
gtcatgaact atatccgtaa cctggatagt gaaacagggg caatggtgcg cctgctggaa     1020
gatggcgatt agtgcgcgcc gccctctcc ctccccccc cctaacgtta ctggccgaag     1080
ccgcttggaa taaggccggt gtgcgtttgt ctatatgtta ttttccacca tattgccgtc     1140
ttttggcaat gtgagggccc ggaaacctgg ccctgtcttc ttgacgagca ttcctagggg     1200
tctttcccct ctcgccaaag gaatgcaagg tctgttgaat gtcgtgaagg aagcagttcc     1260
tctggaagct tcttgaagac aaacaacgtc tgtagcgacc ctttgcaggc agcggaaccc     1320
cccacctggc gacaggtgcc tctgcggcca aaagccacgt gtataagata cacctgcaaa     1380
ggcggcacaa ccccagtgcc acgttgtgag ttggatagtt gtggaaagag tcaaatggct     1440
ctcctcaagc gtattcaaca aggggctgaa ggatgcccag aaggtaccc attgtatggg     1500 atctgatctg gggcctcggt gcacatgctt tacatgtgtt tagtcgaggt taaaaaaacg     1560
tctaggcccc ccgaaccacg gggacgtggt tttcctttga aaaacacgat gataatatgg     1620
ccacaaccat ggtgagcaag ggcgaggagc tgttcaccgg ggtggtgccc atcctggtcg     1680
agctggacgg cgacgtaaac ggccacaagt tcagcgtgtc cggcgagggc gagggcgatg     1740
ccacctacgg caagctgacc ctgaagttca tctgcaccac cggcaagctg cccgtgccct     1800
ggcccaccct cgtgaccacc ctgacctacg gcgtgcagtg cttcagccgc taccccgacc     1860
acatgaagca gcacgacttc ttcaagtccg ccatgcccga aggctacgtc caggagcgca     1920
ccatcttctt caaggacgac ggcaactaca agacccgcgc cgaggtgaag ttcgagggcg     1980
acaccctggt gaaccgcatc gagctgaagg gcatcgactt caaggaggac ggcaacatcc     2040
tggggcacaa gctggagtac aactacaaca gccacaacgt ctatatcatg gccgacaagc     2100
agaagaacgg catcaaggtg aacttcaaga tccgccacaa catcgaggac ggcagcgtgc     2160
agctcgccga ccactaccag cagaacaccc ccatcggcga cggccccgtg ctgctgcccg     2220
acaaccacta cctgagcacc cagtccgccc tgagcaaaga ccccaacgag aagcgcgatc     2280
acatggtcct gctggagttc gtgaccgccg ccgggatcac tctcggcatg gacgagctgt     2340
acaaggatta caaggatgac gacgataag                                      2369
```

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
taaagatatc tcacgtactg acggtg                                            26

<210> SEQ ID NO 3
<211> LENGTH: 24

```
<212> TYPE: DNA
<213> ORGANISM: Artificial Sequence
<220> FEATURE:
<223> OTHER INFORMATION: Primer

<400> SEQUENCE: 3
tctctgacca gagtcatcct tagc                                            24
```